(12) United States Patent
Brockmann et al.

(10) Patent No.: US 12,023,089 B2
(45) Date of Patent: Jul. 2, 2024

(54) RESECTOSCOPE WITH DISTAL ELECTRODE GUIDE

(71) Applicant: OLYMPUS WINTER & IBE GMBH, Hamburg (DE)

(72) Inventors: Christian Brockmann, Hollenstedt (DE); Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 233 days.

(21) Appl. No.: 17/129,436

(22) Filed: Dec. 21, 2020

(65) Prior Publication Data

US 2021/0186595 A1 Jun. 24, 2021

(30) Foreign Application Priority Data

Dec. 20, 2019 (DE) .......................... 102019135571.0

(51) Int. Cl.
*A61B 18/14* (2006.01)
*A61B 17/32* (2006.01)
*A61B 18/00* (2006.01)

(52) U.S. Cl.
CPC ...... *A61B 18/149* (2013.01); *A61B 2017/320052* (2013.01); *A61B 2018/00083* (2013.01); *A61B 2018/00601* (2013.01); *A61B 2018/0091* (2013.01); *A61B 2018/1407* (2013.01)

(58) Field of Classification Search
CPC ....... A61B 18/149; A61B 18/14; A61B 18/12; A61B 18/1492; A61B 2018/1407; A61B 2018/00601; A61B 2018/00083; A61B 2018/0091; A61B 2018/00517; A61B 2018/00982; A61B 2017/320052; A61B 17/00269; A61B 17/32004; A61B 17/320016; A61B 17/32056; A61B 17/32
See application file for complete search history.

(56) References Cited

U.S. PATENT DOCUMENTS

| 3,752,159 | A | | 8/1973 | Wappler | |
|---|---|---|---|---|---|
| 3,939,839 | A | * | 2/1976 | Curtiss | A61B 18/149 600/105 |
| 3,973,568 | A | * | 8/1976 | Iglesias | A61B 18/149 606/46 |
| 4,917,082 | A | | 4/1990 | Grossi et al. | |
| 6,068,603 | A | * | 5/2000 | Suzuki | A61B 10/04 600/564 |

(Continued)

FOREIGN PATENT DOCUMENTS

DE 3918316 A1 3/1990
DE 102017118885 B3 12/2018
(Continued)

*Primary Examiner* — Khadijeh A Vahdat
*Assistant Examiner* — Marina Delaney Templeton
(74) *Attorney, Agent, or Firm* — Oliff PLC

(57) ABSTRACT

A resectoscope for endoscopic surgery with a tubular shaft and a handle, the shaft comprising a longitudinally displaceable electrode instrument and, at its distal end, an electrically insulating insert, the electrode instrument having an elongated shaft section with one or two support arms and, in its distal end region, an electrode that can be acted upon by high-frequency current, characterized in that the insulating insert has one or more guide elements for holding a support arm, the support arm being longitudinally displaceable in the guide element.

12 Claims, 3 Drawing Sheets

(56) References Cited

U.S. PATENT DOCUMENTS

| | | | |
|---|---|---|---|
| 6,358,200 B1 * | 3/2002 | Grossi | A61B 18/24 |
| | | | 600/128 |
| 6,517,498 B1 * | 2/2003 | Burbank | A61B 17/32056 |
| | | | 606/45 |
| 2015/0351826 A1 * | 12/2015 | Kroeber | A61B 1/00087 |
| | | | 600/105 |
| 2019/0150971 A1 * | 5/2019 | Yavari | A61B 17/320016 |
| 2020/0246062 A1 | 8/2020 | Brockmann et al. | |

FOREIGN PATENT DOCUMENTS

| | | |
|---|---|---|
| DE | 102017115377 A1 * | 1/2019 |
| DE | 102017115377 A1 | 1/2019 |
| DE | 10 2019 102 841 A1 | 8/2020 |
| JP | H10-211212 A | 8/1998 |

* cited by examiner

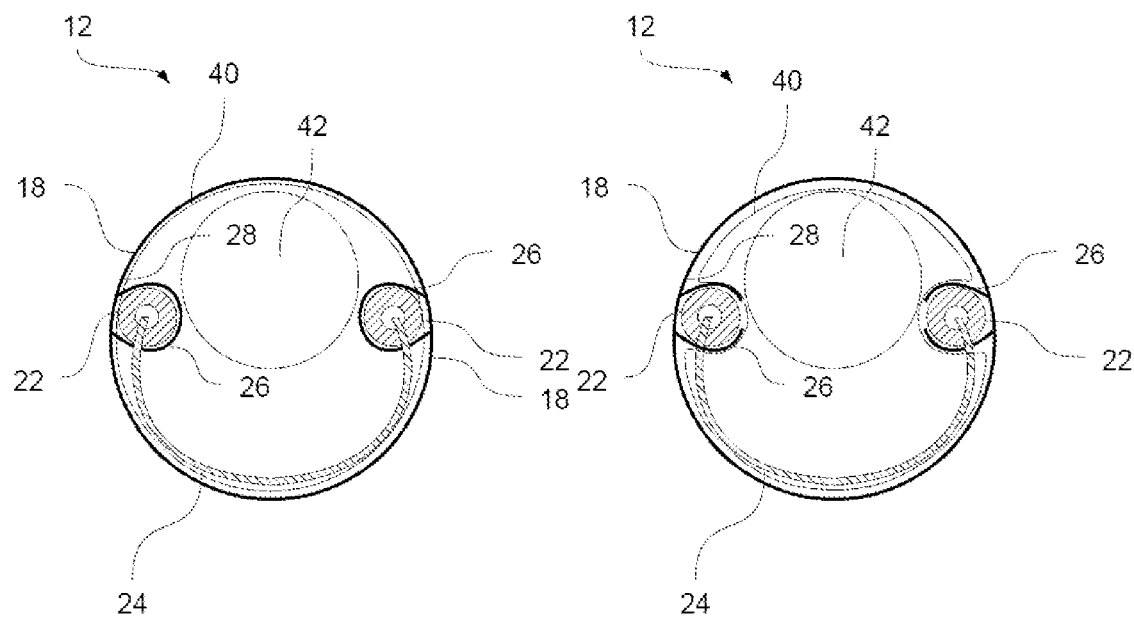
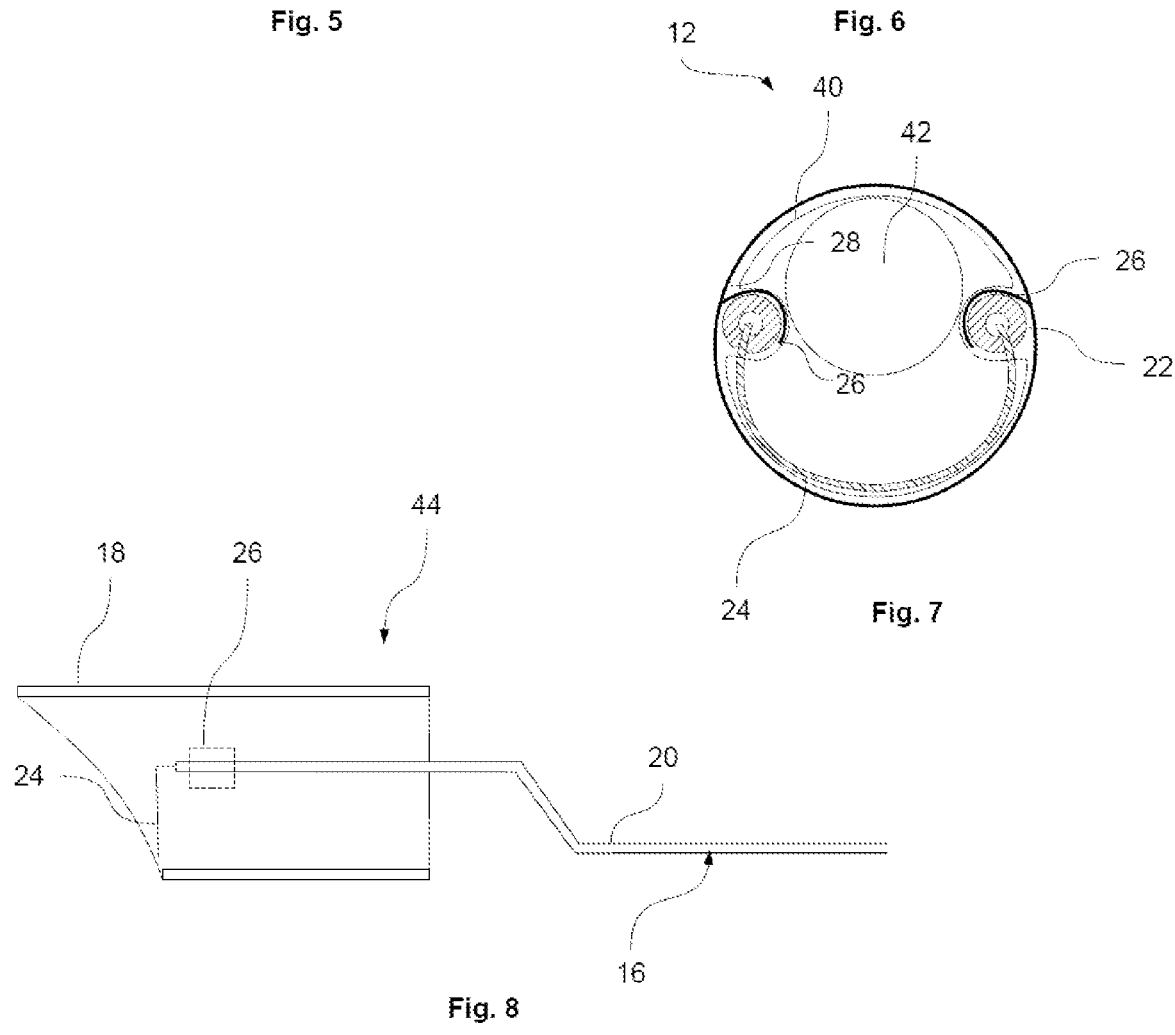

RESECTOSCOPE WITH DISTAL ELECTRODE GUIDE

BACKGROUND

The invention relates to resectoscopes for endoscopic surgery.

Resectoscopes of the generic type are used primarily in urology for surgical work in the bladder and urethra. They are usually used for resection and vaporization of tissue, for example tissue in the lower urinary tract. For this purpose, the resectoscopes comprise a longitudinally displaceable electrosurgical electrode instrument, the distal end of which, after the resectoscope has been inserted, can be pushed out of the distal end of the shaft tube of the resectoscope. In addition, for observing the surgical site and for monitoring the surgical procedure, the resectoscopes usually contain an optical system which comprises an objective at the distal end and which is connected at the proximal end to an eyepiece for direct observation or to an electronic monitoring unit. Finally, to illuminate the surgical site, the resectoscopes contain a lighting element, usually in the form of an optical fiber bundle, which spans the shaft of the resectoscope and is connected at its proximal end to a light source.

At its distal working end, the electrode instrument passed through the resectoscope shaft can comprise an electrosurgical electrode in the form of a loop or a vaporization button (plasma button). Such instruments are, for example, the OES PRO resectoscopes (Olympus), the resectoscopes described in DE 10 2019 102 841 A1 and U.S. Pat. No. 4,917,082 A. The electrode instruments can be designed as bipolar or monopolar instruments, wherein bipolar instruments can have considerable safety advantages over monopolar instruments.

The electrode instruments are longitudinally displaceable in the instrument shaft in order to enable the removal of tissue by means of the distal electrode. In order to ensure straight guidance of the electrode instruments through the instrument shaft, the electrode instruments generally have guide elements on their elongated shaft segment which support the electrode instrument on the surface of the optics or on an inner wall of the resectoscope shaft. For this purpose, the guide elements are usually designed to be complementary to the optics or the inner wall, for example in the form of partially circular guide plates.

Since the usual electrode instruments have a relatively long stroke of, for example, 23 mm, the guide elements are usually just as far apart from the distal end of the electrode instrument. This ensures that the guide elements also remain within the resectoscope shaft when the electrode instrument is displaced as far as possible distally. However, the result of this wide distance between the guide elements and the distal electrode is that the electrode instrument can be bent in this region and the electrode can therefore shift or even bend relative to the resectoscope shaft. In addition, the positioning of distally bent electrode instruments cannot be corrected.

Since the distal end of the resectoscope shaft is often used as a cutting edge for tissue during surgical interventions, it is important, however, that the electrode position can be guided exactly to the edge of the distal end of the resectoscope shaft. This is the only way to achieve a good cutting result. Even minor inaccuracies in the straightness of the electrode instruments can have negative effects on the cutting properties of the electrode instruments. If a loop electrode is too deep, direct contact between the electrode and the shaft tip can damage the electrode. For example, when the loop is pulled out, it can get caught on the shaft tip or an insulating attachment and bend or even break. It is also possible for material damage to the shaft to occur. If a loop electrode is too high, the resectoscope shaft can be omitted as a cutting edge and cutting off tissue is made more difficult, at least.

The object of the present invention is therefore to provide a resectoscope whose electrode instruments are more strongly stabilized in their distal end region.

DESCRIPTION

This object is achieved using a resectoscope and electrode system according to the disclosed embodiments.

In a first aspect, the invention relates in particular to a resectoscope for endoscopic surgery with a tubular shaft and a handle, the shaft comprising a longitudinally displaceable electrode instrument and, at its distal end, an electrically insulating insert, the electrode instrument having an elongated shaft segment with one or two support arms and, in its distal end region, an electrode that can be acted upon by high-frequency current, characterized in that the insulating insert has one or more guide elements for holding a support arm, the support arm being longitudinally displaceable in the respective guide element.

The inventive arrangement of the stabilizing guide elements in the insulating insert at the distal end of the resectoscope shaft minimizes the distance between the electrode tip and the guide elements, which enables more secure positioning of the electrode. When the electrode instrument is moved longitudinally, the guide elements are no longer moved with it. As a result, the electrode system is significantly more stable overall and protected against bending. In addition, more precise cuts with slightly bent electrode instruments are also possible, since the electrodes are guided by the guide elements into the correct position to the cutting edge of the shaft end when cutting. The cutting result is thus significantly improved overall.

In a usual embodiment, the inventive resectoscope has a tubular shaft. The endoscope shaft comprises an elongated jacket tube. In addition to the shaft part, the resectoscope includes a handle for holding and operating, which handle usually comprises two handle parts.

The shaft of the resectoscope has an electrode instrument arranged to be longitudinally displaceable. The electrode instrument is used as a pass-through instrument in such a resectoscope and can be designed for single or multiple use.

The electrode instrument has an elongated shaft segment (shaft part) and is designed as a pass-through instrument for a resectoscope, i.e. as an instrument that can be inserted into a body opening through a resectoscopic shaft tube. At its distal end, the electrode instrument has an electrode that can be subjected to high-frequency current. The electrode can be a cutting loop, a vaporization button (plasma button), or other commercially available electrodes. The electrode is preferably a cutting loop electrode. Corresponding electrodes and electrode instruments are known to those skilled in the art.

The electrode instrument can be a bipolar electrode instrument that includes the electrode as part of an electrode arrangement. In this case, the electrode instrument will comprise, for example, a second electrode in the distal end region of the electrode instrument which is designed as a neutral electrode. Alternatively, the second electrode (neutral electrode) can also be arranged on other elements of the distal end region of the resectoscope. Of course, the electrode instrument can also be designed as a monopolar instrument.

The electrode instrument is longitudinally displaceable within the shaft of a resectoscope, i.e. it can be moved in the axial direction distally and proximally. To connect to the resectoscope, the electrode instrument has the elongated shaft, which can be attached at its proximal end to a carriage encompassed by the resectoscope in order to produce a movement-coupled connection. The carriage typically slides on a tube and is held in a rest position in a spring-loaded manner via a spring unit. Thus, at its distal end the electrode can be moved toward or away from the tissue to be cut without having to move the entire resectoscope. In addition, the longitudinal displaceability of the electrode instrument makes it possible to clamp tissue between the electrode and the insulating insert and to remove it from the surgical site. The distal end of the resectoscope shaft or insulating insert and the electrode are thus movable toward and away from one another by means of the longitudinal displaceability of the electrode instrument.

The electrode instrument has one or two elongated support arms which form the shaft segment of the electrode instrument. Electrode instruments with two support arms are preferred according to the invention. If the electrode instrument has only one support arm, the electrode is arranged at its distal end. If the electrode instrument has two support arms, these are connected to one another at their distal end by a connecting element. The connecting element can embody the electrode, for example, or the electrode can be arranged on the connecting element. In other words, the support arms support the electrode or a connecting element that supports the electrode. The support arm or arms are preferably elongated. If the electrode instrument has two support arms, these run essentially parallel to one another. The two support arms can run, for example, along the inner wall of an inner tube or jacket tube of the resectoscope and be spaced from one another along the inner circumference of this inner wall by about 120° to 200°, preferably about 180°. It is therefore preferred that the two support arms are approximately opposite one another, the longitudinal axis of the resectoscope shaft representing the center point between the two support arms.

In addition to the electrode instrument, the shaft of the resectoscope has an insulating insert at its distal end. The insulating insert is electrically non-conductive, i.e. electrically insulating. This assures insulation of the active electrode from the conductive resectoscope shaft. For this purpose, the insulating insert is preferably made entirely, but at least to an extent that ensures its insulating ability, of an electrically non-conductive material, i.e., electrically insulating material. Such materials are known to those skilled in the art and include, for example, ceramics and plastics. Insulation inserts made of plastics are particularly preferred according to the invention because of the relatively low production costs and good insulation properties. Since the insulating insert can come into contact with the resulting plasma during electrosurgical treatment with an electrode, thermostable plastics are particularly preferred. Thermostable plastics are able to withstand with no damage the high temperatures that arise in the region of the distal resectoscope tip. Suitable thermostable plastics can be selected, for example, from the group comprising fluoropolymers and cycloolefin copolymers. The insulating inserts made of plastic can be manufactured by means of an injection molding process.

The insulating insert is suitable for a detachable connection to the distal end region of a resectoscope shaft. This means that the insulating insert and the end region are at least partially complementary in shape and size. As a result, the insulating insert can be connected to the end region. In any case, the connection is strong and secure enough that the isolation insert is prevented from becoming detached during an operative intervention. For example, the insulating insert, which has a cylindrical segment, can be pushed onto the inner tube or jacket tube, pushed into the inner tube, or pushed between the inner tube and jacket tube.

The insulating insert has a hollow segment with an elongated cavity for passing through pass-through instruments. This segment is arranged in the proximal end region of the insulating insert. It ensures that pass-through instruments guided through the resectoscope shaft can be passed through the channel-shaped interior of the insulating insert. The insulating insert can have a substantially cylindrical shape or at least a substantially cylindrical proximal segment. Correspondingly, the cavity in the interior of the hollow segment can have a hollow cylindrical shape.

The inventive insulating insert has one or more guide elements for holding a support arm, i.e. 1, 2, or more guide elements. Insulating inserts with two guide elements are preferred according to the invention. In other words, each guide element is designed to hold a support arm. If the electrode instrument has two support arms, the insulating insert will also comprise two corresponding guide elements. On the other hand, if the electrode instrument has only one support arm, the insulating insert comprises only one corresponding guide element.

Within the guide element, the support arm assigned to the guide element is mounted in a longitudinally displaceable manner, i.e. held such that the support arm and thus also the electrode instrument can be displaced in the longitudinal direction of the resectoscope shaft. At the same time, the guide element prevents the support arm from being displaced in other directions, i.e. in directions which deviate from the longitudinal direction of the resectoscope shaft, for example transversely to the longitudinal direction (radially).

In order to stabilize the electrode instrument, the guide element or elements are arranged as close as possible on the distal shaft end or end of the insulating insert. The distance between the distal end of the shaft and the guide element or elements can be, for example, 1.5 cm or less, 1 cm or less, 0.5 cm or less, 0.25 cm or less. The distance is preferably 0.5 cm or less.

The guide element or elements are arranged on the inner wall of the insulating insert. The guide elements are arranged and designed such that they do not obstruct or only insignificantly obstruct the viewing axis of the optics. The guide elements are usually formed approximately parallel to the longitudinal axis (LS) of the resectoscope shaft, i.e. the longitudinal axes (LF) of the guide element or elements are each approximately parallel to the longitudinal axis (LS) of the shaft. At the same time, the guide elements extend from the inner wall of the insulating insert into the interior of the insulating insert, preferably at an angle of 140° to 40°, preferably at an angle of 110° to 70°, more preferably at an angle of about 90°, in relation to the inner wall of the insulating insert. The guide elements preferably do not extend into a region of the interior that is located distal from the optics or distal from the distal end of one of the support arms.

The guide elements can be made of the same insulating material as the insulating insert, i.e. a ceramic, for example. Alternatively, however, guide elements made of the thermostable plastics described above are also possible. It is preferred that the guide elements are formed in one piece with the rest of the insulating insert.

As already explained elsewhere herein, the guide element or elements enclose the respective support arm such that longitudinal displacement of the support arm is ensured and, at the same time, displacement of the support arm in other directions, e.g. transverse to the longitudinal direction of the resectoscope shaft, is prevented. This can be achieved in that the guide element encloses the respective support arm over 90° or more of its circumference, preferably over 180° or more, for example 240° or more. For simple assembly of an electrode in a shaft with a permanently installed insulating insert, however, it can be advantageous if the degree of enclosure is kept low. A part of the inner wall of the insulating insert, which also encloses the respective support arm, is regarded as part of the guide element. Thus, if the inner wall of the insulating insert borders the outer circumference of the support arm over 20° and an extrusion protruding from the inner wall borders a further 120° of the support arm, the guide element formed from a part of the inner wall and the extrusion surrounds the support arm over 140°.

In one embodiment it is provided that the guide element does not completely surround the support arm assigned to it. In this way, if necessary, the support arm can be led out of the guide element laterally and can also be inserted laterally into the guide element for assembly. For this purpose, the guide element can have sufficient flexibility to guide the support arm out of the element by slightly bending the element. In this embodiment, the guide element encloses the support arm over 90° to 240° of its circumference, preferably over 180° to 240°. This embodiment is particularly suitable for mounting the electrode instrument in a resectoscope that has an insulating insert that is securely connected to the resectoscope shaft. The electrode instrument can be designed for single use, while the rest of the resectoscope, including the insulating insert, can be designed for multiple use and reprocessing (cleaning).

In an alternative embodiment, the guide element is enclosed by the support arm such that the support arm cannot be removed from the guide element without damaging the guide element. This can be useful, for example, if the insulating insert is to be part of the electrode system designed for a single use. In this embodiment, the insulating insert is likewise designed for single use. In this and other embodiments, the guide element surrounds the respective support arm over 180° or more of its circumference, preferably over 240° or more, for example over 360°, i.e. completely.

Accordingly, in a related aspect, the invention also relates to an electrode system, preferably designed for single use, for use in a resectoscope for endoscopic surgery, which comprises an insulating insert and an electrode instrument described herein. Specifically, this aspect relates to an electrode system which is characterized in that it comprises an electrode instrument and an electrically insulating insert, the electrode instrument having an elongated shaft segment with one or two support arms and, in its distal end region, an electrode that can be acted upon by high-frequency current, and the insulating insert having one or more guide elements for holding one support arm of the electrode instrument, the support arm being arranged in the guide element so as to be longitudinally displaceable.

The electrode system can be used in an inventive resectoscope, but it can be sold separately from the resectoscope. The electrode system can therefore be designed for single use, for example.

The guide element or elements of the electrode system surround the respective support arm over 180° or more of its circumference, preferably 240° or more, most preferably 360°.

BRIEF DESCRIPTION OF THE FIGURES

Exemplary embodiments of the invention are shown schematically in the drawings. The figures are as follows:

FIG. 5 is a schematic front view of the shaft of a resectoscope according to the invention, which has an insulating insert with guide elements for the support arms of an electrode instrument;

FIG. 6 is a schematic front view of the shaft of an alternative resectoscope according to the invention, which has an insulating insert with guide elements for the support arms of an electrode instrument and in which the support arms run between inner tube and jacket tube and in which the guide elements do not completely enclose the support arms;

FIG. 7 is a schematic front view of the shaft of an alternative resectoscope according to the invention, which has an insulating insert with guide elements for the support arms of an electrode instrument and in which the support arms run between inner tube and jacket tube and in which the guide elements do not completely enclose the support arms; and, FIG. 8 is a lateral, schematic sectional illustration of the distal end region of an electrode system according to the invention, which comprises an insulating insert with guide elements (shown in dashed lines) for the support arms of an electrode instrument and a corresponding electrode instrument.

EXEMPLARY EMBODIMENTS

Further advantages, characteristics and features of the present invention will become apparent in the following detailed description of exemplary embodiments with reference to the accompanying drawings. However, the invention is not restricted to these exemplary embodiments.

Figure 1:
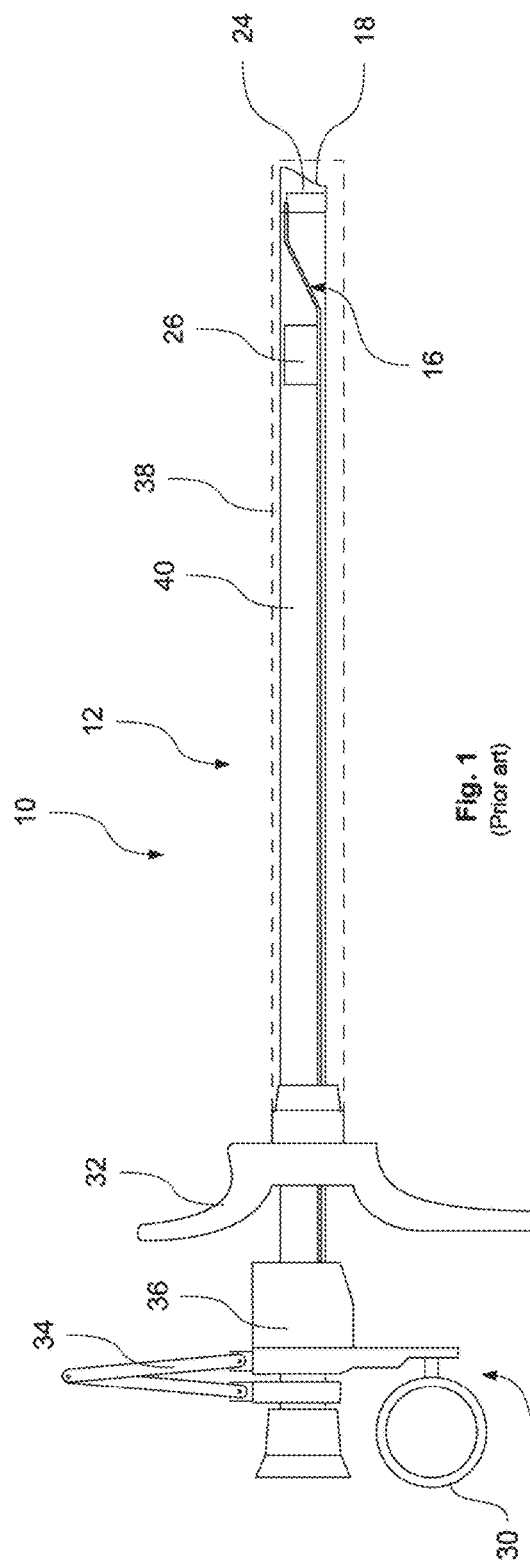
FIG. 1 is a lateral, schematic sectional illustration of a resectoscope from the prior art, which comprises an electrode instrument with guide elements which are attached to the electrode instrument.
Figure 3:
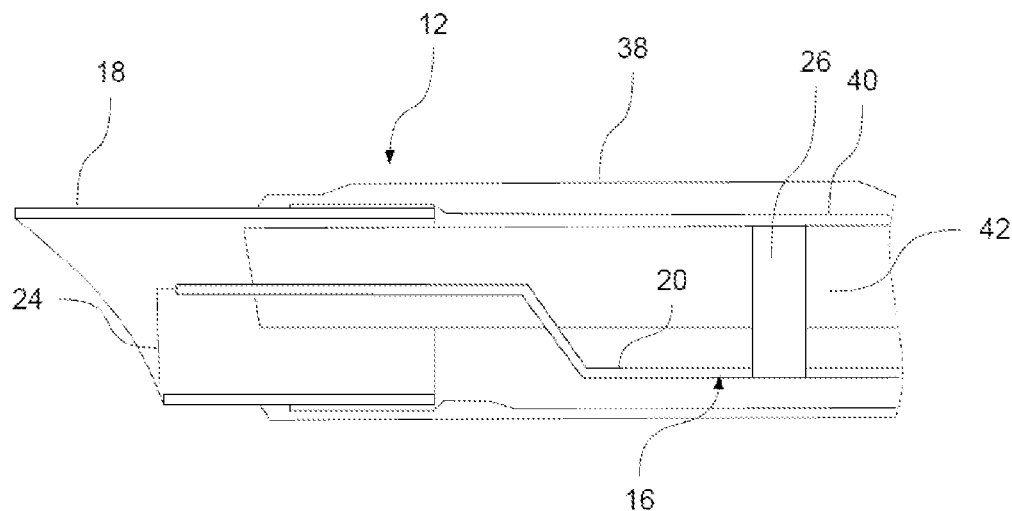
FIG. 3 is a lateral, schematic sectional illustration of the distal end region of a resectoscope from the prior art, which comprises an electrode instrument with guide elements which are attached to the electrode instrument and which are supported on the optics of the system.

FIG. 1 shows a schematic, lateral sectional illustration of a resectoscope 10 from the prior art in which arranged on the inner tube 40 is an insulating insert 18 and guide elements 26 are arranged on the electrode instrument 16 thereof and are supported on optics (not shown) inside the inner tube 40. FIG. 3 shows a schematic, lateral sectional illustration of the distal end region of the same resectoscope 10 from the prior art.

The resectoscope 10 has a shaft 12 which comprises a jacket tube 38 (outer tube) shown in dashed lines. An inner tube 40 runs inside the jacket tube 38 and an electrode instrument 16 runs inside the inner tube 40, as well as optics 42 shown in FIG. 3 and a lighting means (not shown), for example in the form of an optical fiber bundle. In addition, other elements, not shown here, can run in the resectoscopes, such as a separate irrigation tube and the like. In its distal end region, the jacket tube 38 includes openings through which the contaminated irrigation fluid can flow into the space between jacket tube 38 and inner tube 40 and flow away through the resectoscope shaft 12.

As can be seen in FIG. 1 and in greater detail in FIG. 3, an electrode instrument 16 in this conventional instrument is to be protected against displacements deviating from the longitudinal direction of the shaft 12, for example transverse to the longitudinal direction, by means of a guide element 26 with a partially circular cross-section. The electrode instrument 16 is borne in the inner tube 40 so as to be longitudinally displaceable. The guide element 26 has a shape complementary to the outer wall of the optics 42 and has a partially cylindrical shape. The guide element 26 is fastened in a shaft segment 20 of the electrode instrument 16 to two support arms (fork tubes) 22 (FIG. 5). The support arms 22 run close to one another within the resectoscope shaft 12 and only diverge from one another in the distal end region of the resectoscope shaft 12 in order to receive and support between their ends an electrode 24 in the form of a loop electrode. The guide elements 26 of the electrode instrument 16 do not help prevent bending of the electrode instrument 16 in the region which is located distal from the guide elements 26.

The electrode instrument 16 can be moved axially in the distal and proximal direction by actuation of a handle 14 in a forcibly guided manner. It can be pushed beyond the distal end of the inner tube 40 and jacket tube 38. This enables the surgeon to manipulate tissue further away from the resectoscope tip. For this purpose, the inner tube 40 and/or electrode instrument 16 are also borne rotatable about their longitudinal axis. At its distal end, the electrode instrument 16 has an electrode 24 which is designed as a cutting loop and by means of which tissue can be removed by electrosurgical ablation. Here, a high-frequency electrical voltage is applied to the electrode 24 in order to cut tissue.

The resectoscope 10 shown has a passive transporter, in which the carriage 36 is displaced in the distal direction against the distal, first handle part 32 by a relative movement of the handle parts 30 and 32 arranged proximally from the resectoscope shaft on the handle 12 against a spring force applied by a spring bridge 34. When the carriage 36 is displaced in the distal direction against the handle part 32, the electrode instrument 16 is displaced in a positively guided manner in the distal direction in a manner not shown. When the handle parts 30, 32 are relieved, the spring force generated by the spring bridge 34 forces the carriage 36 back into its rest position, the electrode instrument 16 being pulled in the proximal direction. When the carriage 36 is moved back, an electrosurgical intervention with the electrode instrument 16 can be carried out without manual force from the surgeon, that is to say, passively.

The insulating insert 18 of the resectoscope 10 is non-detachably connected to the distal end of to the latter by an adhesive bond. The insulating insert 18 does not contain any guide elements. It is made of an electrically insulating ceramic.

Figure 2:
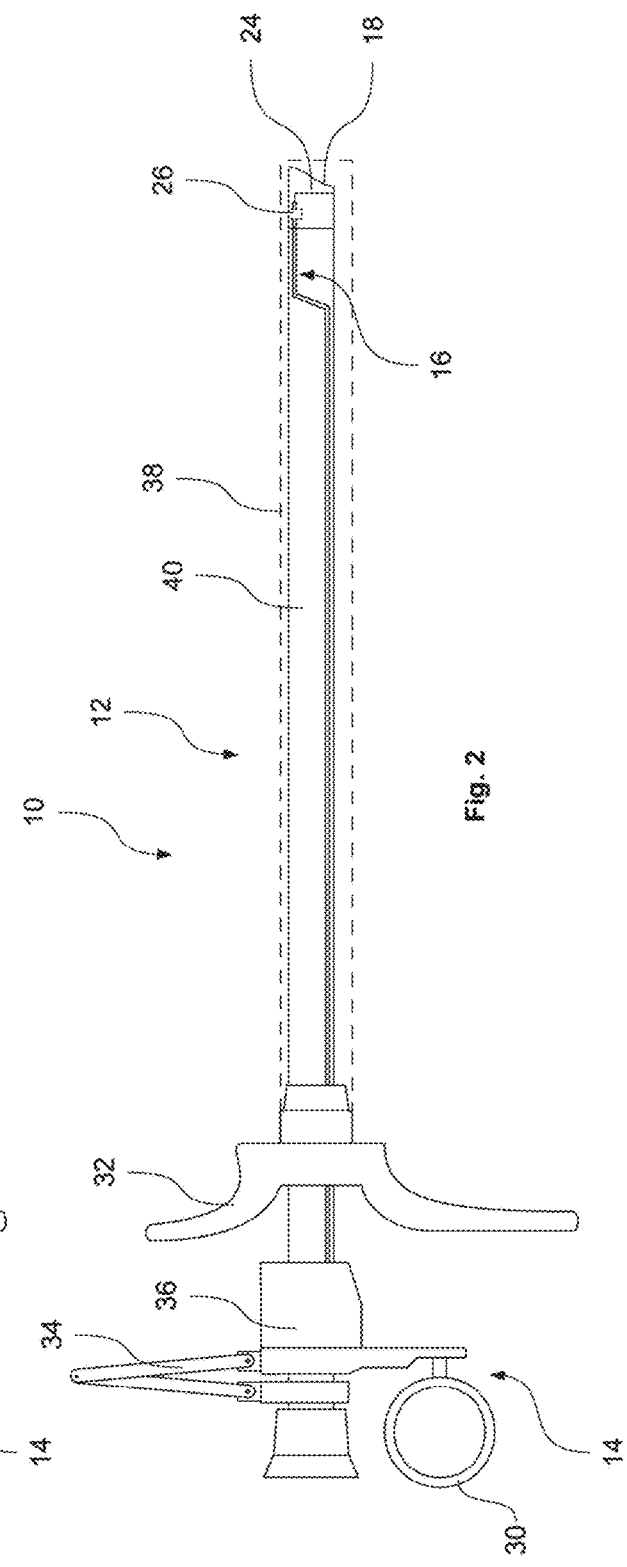
FIG. 2 is a lateral, schematic sectional illustration of a resectoscope according to the invention, which has an insulating insert with guide elements for the support arms of an electrode instrument.
Figure 4:
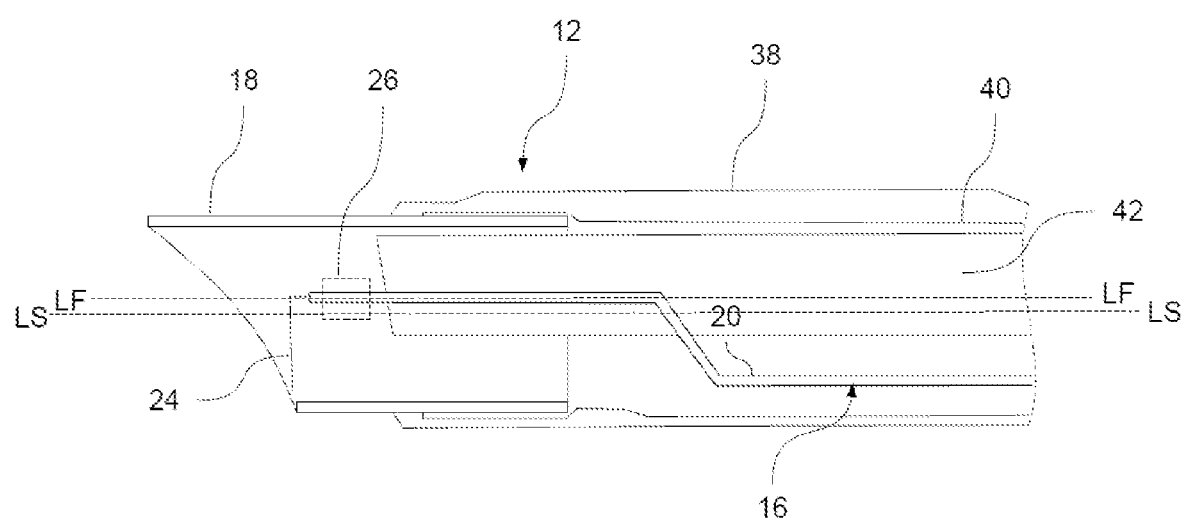
FIG. 4 is a lateral, schematic sectional illustration of the distal end region of a resectoscope according to the invention, which has an insulating insert with guide elements (shown in dashed lines) for the support arms of an electrode instrument.

FIG. 2 and FIG. 4 show schematic, lateral sectional illustrations of a resectoscope 10 according to the invention.

The resectoscope 10 according to the invention differs from that shown in FIG. 1 and FIG. 3 in that the guide elements 26 for stabilizing the longitudinal movement of the electrode instrument 16 are not arranged on the shaft segment 20 of the electrode instrument 16, but on the inner wall 28 of the insulating insert 18. By attaching the guide elements 26 inside the insulating insert 18, the maximum distance between the guide elements 26 and the electrode 24 is reduced to a minimum. This significantly reduces the risk of the distal end region of the electrode instrument 16 being bent, even if the electrode instrument 16 is displaced maximally in the distal direction. The guide elements 26 are spaced approximately 0.5 cm from the distal end of the insulating insert 18. The longitudinal axis of the guide element (LF) is approximately parallel to the longitudinal axis of the shaft part (LS). In FIG. 4 it can be seen that the guide elements 26 are elongated in the longitudinal direction of the shaft 12.

In FIG. 5, which shows parts of the same resectoscope 10 as in FIG. 2 and FIG. 4, namely a schematic front view of the shaft 12, it can be seen that the electrode instrument 16 has two support arms 22, between the distal ends of which an electrode 24 which has the shape of a loop electrode is held. The support arms 22 are traversed in their interior by a conductive wire and also comprise an insulating layer which encases the wire and which electrically insulates the support arms 22 from the outside. The inner tube 40 also has optics 42 which run between the support arms 22.

It can also be seen that the insulating insert 18, which is arranged at the distal end of the resectoscope shaft 12, has two guide elements 26. The guide elements 26 lie opposite one another as viewed from the sagittal plane of the insulating insert 18. Each of the two support arms 22 of the electrode instrument 16 runs through a guide element 26 of the insulating insert 18. In order to save space, the guide elements 26 are at least partially complementary in shape to the support arms 22. The guide elements 26 each have a partial circular shape, and their ends are connected to the inner wall 28 of the insulating insert 18. In the embodiment shown, the guide elements 26 are formed in one piece with the insulating insert 18 from an electrically insulating ceramic. The guide elements 26 completely surround the respective support arm 22, i.e. over 360° of its circumference.

FIG. 6 shows a schematic front view of the shaft 12 of an alternative resectoscope 10 according to the invention, which has an insulating insert 18 with guide elements 26 for the support arms 22 of an electrode instrument 16. The resectoscope 10 differs from that shown in FIG. 5 in that the support arms 22 of the electrode instrument 16 are not arranged within the inner tube 40, but instead are arranged between the inner tube 40 and the jacket tube 38. In addition, in contrast to those shown in FIG. 5, the guide elements 26 do not completely enclose the support arms 22. The guide elements 26 each have an interruption which can be used for laterally introducing the support arms 22. For this purpose, the guide elements 26 are sufficiently flexible to allow the interruption to be enlarged during assembly or disassembly without bending or breaking. In the embodiment shown, the interruption in the guide elements 26 is formed in the direction of the optics or in the direction of the second support arm 22. The interruptions in the two guide elements 26 thus lie opposite one another. The interruptions extend in a manner not shown here in the longitudinal direction of the instrument over the entire length of the guide elements 26.

FIG. 7 shows an alternative design to FIG. 6 for support arms 22 which are not designed to completely enclose guide elements 26. The guide elements 26 each have an interruption here, as well. The interruption is formed in the direction of a transverse plane of the resectoscope shaft 12. The interruptions extend in a manner not shown here in the longitudinal direction of the instrument over the entire length of the guide elements 26.

FIG. 8 is a lateral, schematic sectional illustration of the distal end region of an electrode system 44 according to the invention, which comprises an insulating insert 18 with guide elements 26 (shown in dashed lines) for the support arms 22 of an electrode instrument 16 and a corresponding electrode instrument 16. The electrode system 44 is designed for single use and can be disposed of after use in a medical procedure. Alternatively, an electrode system 44 designed for multiple use is also possible. The insulating insert 18 in the electrode system 44 facilitates the assembly of the electrode system on the resectoscope shaft 12, since the insulating insert 18, in contrast to the sensitive electrode instrument 16, can be touched during assembly without the risk of bending. The insulating insert 18 can include latching mechanisms (not shown here) or other fastening means for fastening, such as the fastening means described in DE 10 2019 102 841.8. In this case, the guide elements 26 are designed to completely enclose the respective support arm 22.

Although the present invention has been described in detail with reference to the exemplary embodiments, it is obvious to the person skilled in the art that the invention is not restricted to these exemplary embodiments, but rather that modifications are possible in such a way that individual features may be omitted or other combinations of the individual features presented may be realized, provided the scope of protection of the appended claims is not exceeded. The present disclosure includes all combinations of the individual features presented.

The invention claimed is:

1. A resectoscope for endoscopic surgery, the resectoscope comprising:
   a handle; and
   a tubular shaft comprising:
     a longitudinally displaceable electrode instrument comprising:
       an elongated shaft section with a first support arm and a second support arm; and
       an electrode positioned in a distal end region of the electrode instrument and that can be acted upon with high-frequency current; and
     an electrically insulating insert provided at a distal end of the electrode instrument, the insulating insert comprising:
       a first guide element for holding the first support arm of the electrode instrument, the first support arm being longitudinally displaceable in the first guide element; and
       a second guide element for holding the second support arm of the electrode instrument, the second support arm being longitudinally displaceable in the second guide element,
     wherein the first and second guide elements are arranged on, in direct contact with and fixed to the inner wall of the insulating insert.

2. The resectoscope according to claim 1, wherein the distance between the distal end of the shaft and the first and second guide elements is 1 cm or less.

3. The resectoscope according to claim 1, wherein the longitudinal axes of the first and second guide elements run parallel to the longitudinal axis of the shaft.

4. The resectoscope according to claim 1, wherein:
   the first guide element encloses the first support arm over at least 90° and no more than 360° of its circumference, and
   the second guide element encloses the second support arm over at least 90° and no more than 360° of its circumference.

5. The resectoscope according to claim 1, wherein:
   the first guide element encloses the first support arm over at least 240° and no more than 360° of its circumference, and
   the second guide element encloses the second support arm over at least 240° and no more than 360° of its circumference.

6. The resectoscope according to claim 1, wherein the electrode is a loop electrode.

7. The resectoscope according to claim 1, wherein the first and second guide elements are formed in one piece with the inner wall of the insulating insert.

8. The resectoscope according to claim 1, wherein:
   the first guide element does not completely enclose the first support arm over its circumference, and
   the second guide element does not completely enclose the second support arm over its circumference.

9. An electrode system for use in a resectoscope for endoscopic surgery, the electrode system comprising:
   an electrode instrument comprising:
     an elongated shaft section with a first support arm and a second support arm; and
     an electrode positioned in a distal end region of the electrode instrument and that can be charged with high-frequency current; and
   an electrically insulating insert provided at a distal end of the electrode instrument, the insulating insert comprising:
     a first guide element for holding the first support arm of the electrode instrument, the first support arm being arranged in the first guide element so as to be longitudinally displaceable; and
     a second guide element for holding the second support arm of the electrode instrument, the second support arm being longitudinally displaceable in the second guide element,
   wherein the first and second guide elements are arranged on, in direct contact with and fixed to the inner wall of the insulating insert.

10. The electrode system according to claim 9, wherein:
    the first guide element surrounds the first support arm over at least 240° and no more than 360° of its circumference, and
    the second guide element surrounds the second support arm over at least 240° and no more than 360° of its circumference.

11. The electrode system according to claim 9, wherein the first and second guide elements are formed in one piece with the inner wall of the insulating insert.

12. The electrode system according to claim 9, wherein:
    the first guide element does not completely enclose the first support arm over its circumference, and
    the second guide element does not completely enclose the second support arm over its circumference.

* * * * *